US006875590B2

(12) United States Patent
Chen et al.

(10) Patent No.: US 6,875,590 B2
(45) Date of Patent: Apr. 5, 2005

(54) LEADER PEPTIDES FOR ENHANCING SECRETION OF RECOMBINANT PROTEIN FROM A HOST CELL

(75) Inventors: Tseng-hui Timothy Chen, Burlingame, CA (US); Brian Schmidt, Half Moon Bay, CA (US)

(73) Assignee: Corixa Corporation, Seattle, WA (US)

( * ) Notice: Subject to any disclaimer, the term of this patent is extended or adjusted under 35 U.S.C. 154(b) by 186 days.

(21) Appl. No.: 09/875,494

(22) Filed: Jun. 5, 2001

(65) Prior Publication Data

US 2002/0072093 A1 Jun. 13, 2002

Related U.S. Application Data

(60) Provisional application No. 60/209,517, filed on Jun. 5, 2000.

(51) Int. Cl.[7] .......................... C12P 21/00; C07H 21/04

(52) U.S. Cl. ............................. 435/69.7; 435/4; 435/6; 435/69.1; 435/69.8; 435/71.1; 435/320.1; 536/23.1; 536/23.4; 536/23.53

(58) Field of Search .............................. 536/23.1, 23.4, 536/23.53; 435/4, 6, 69.1, 69.7, 69.8, 71.1, 320.1

(56) References Cited

U.S. PATENT DOCUMENTS

| | | | | |
|---|---|---|---|---|
| 4,757,013 A | | 7/1988 | Inouye | |
| 5,470,719 A | | 11/1995 | Meng | |
| 5,747,662 A | | 5/1998 | Simmons | |
| 5,840,523 A | | 11/1998 | Simmons | |
| 2002/0082411 A1 | * | 6/2002 | Carter et al. | 536/23.5 |

FOREIGN PATENT DOCUMENTS

| | | |
|---|---|---|
| EP | 0 731 167 A | 9/1996 |
| WO | WO 01 70245 A | 9/2001 |

OTHER PUBLICATIONS

Skerra et al. Assembly of a functional immunoglobulin Fv fragment in *Escherichia coli*. Science 240:1038–1041, 1988.*

Gennity et al. (1990) J. Bioeng. Biomemb. 22:233–269.

Izard et al. (1995) Biochemistry 34:9904–9912.

Izard et al. (1996) The Journal of Biological Chemistry 271:35:21579–21582.

Klein et al. (1992) Prot. Eng. 5:511–517.

Miller et al. (1998) J. Biol. Chem. 273:19:11409–11412.

Nielsen et al. (1997) Prot. Eng. 10:1:1–6.

Pugsley (1993) Microbiol. Rev. 57:50–108.

Rusch et al. (1994) Journal of Cellular Biochemistry 35:209–217.

Simmons et al. (1996) Nature Biotechnology 14:629–634.

Carter P et al., "Humanization of an Anti–P185HER2 Antibody for Human Cancer Therapy", Proceedings of the National Academy of Sciences of USA, National Academy of Science. Washington, US, vol. 89, No. 10, (May 15, 1992), pp. 4285–4289, XP000275844.

Chung Nan Chang et al., "High–Level Secretion of Human Growth Hormone by *Escherichia coli*", Gene, Elsevier Biomedical Press, Amsterdam, NL, vol. 55, 1987, pp. 189–196, XP002006630.

Picken R N et al., "Nucleotri'.e Sequence of the Gene for Heat Stable Enter0 Toxin II of *E scherichia–coli*", Infection and Immunity, vol. 42, No. 1, 1983, pp. 269–275, XP002202262.

Skerra A et al., "Assembly of a Functional Immunoglobulin FV Fragment I N *Escherichia coli*", Science, American Association for the Advancement of Science, US, vol. 240, 1988, pp. 1038–1041, XP002947104.

Ueda Y et al., "Synthesis and Expression of a DNA Encoding the FV Dohain of an Anti–Lysozyme Monoclonal Antibody, Hyhelio, In Streptomyces Lividans", Gene, Elsevier Biomedical Press. Amsterdam, NL, vol. 129, 1993, pp. 129–134, XP00200820.

* cited by examiner

*Primary Examiner*—James Ketter
*Assistant Examiner*—David A. Lambertson
(74) *Attorney, Agent, or Firm*—Kristen K. Walker

(57) ABSTRACT

Novel synthetic leader peptides have been identified. The leader peptides have use in a method of enhancing the secretion of a recombinant polypeptide produced in a host cell. Polynucleotides encoding the novel leader peptides and a method of designing the polynucleotides are described.

21 Claims, 6 Drawing Sheets pBAD2B1A-vk1-vh3

SEQUENCE LISTING

```
<160> NUMBER OF SEQ ID NOS: 25

<210> SEQ ID NO 1
<211> LENGTH: 24
<212> TYPE: PRT
<213> ORGANISM: Artificial Sequence
<220> FEATURE:
<223> OTHER INFORMATION: synthetic peptide

<400> SEQUENCE: 1

Met Ala Lys Lys Asn Ser Thr Leu Leu Val Ala Val Ala Ala Leu Ile
1               5                   10                  15

Phe Met Ala Gly Arg Ala Asn Ala
            20

<210> SEQ ID NO 2
```

-continued

<211> LENGTH: 24
<212> TYPE: PRT
<213> ORGANISM: Artificial Sequence
<220> FEATURE:
<223> OTHER INFORMATION: synthetic peptide

<400> SEQUENCE: 2

```
Met Ala Lys Lys Asn Ser Thr Leu Leu Val Ala Val Ala Ala Leu Ile
1               5                   10                  15

Met Phe Thr Gln Pro Ala Asn Ala
            20
```

<210> SEQ ID NO 3
<211> LENGTH: 24
<212> TYPE: PRT
<213> ORGANISM: Artificial Sequence
<220> FEATURE:
<223> OTHER INFORMATION: synthetic peptide

<400> SEQUENCE: 3

```
Met Gly Lys Lys Gln Thr Ala Val Ala Phe Ala Leu Ala Leu Leu Ala
1               5                   10                  15

Leu Ser Met Thr Pro Ala Tyr Ala
            20
```

<210> SEQ ID NO 4
<211> LENGTH: 24
<212> TYPE: PRT
<213> ORGANISM: Artificial Sequence
<220> FEATURE:
<223> OTHER INFORMATION: synthetic peptide

<400> SEQUENCE: 4

```
Met Gly Arg Lys Gln Thr Ala Val Ala Phe Ala Leu Ala Leu Leu Ser
1               5                   10                  15

Leu Ala Phe Thr Asn Ala Tyr Ala
            20
```

<210> SEQ ID NO 5
<211> LENGTH: 106
<212> TYPE: DNA
<213> ORGANISM: Artificial Sequence
<220> FEATURE:
<223> OTHER INFORMATION: synthetic

<400> SEQUENCE: 5

```
acccgttttt ttgggctaac aggaggaatt aaccatggct aaaaagaact ccaccctgct     60

cgttgcagta gctgcgctga tcttcatggc cggaagggcc aacgct                   106
```

<210> SEQ ID NO 6
<211> LENGTH: 106
<212> TYPE: DNA
<213> ORGANISM: Artificial Sequence
<220> FEATURE:
<223> OTHER INFORMATION: synthetic

<400> SEQUENCE: 6

```
acccgttttt ttgggctaac aggaggaatt aaccatggct aaaaagaact ccaccctgct     60

cgttgcagta gctgcgctta tcatgttcac tcagccggcg aacgct                   106
```

<210> SEQ ID NO 7
<211> LENGTH: 106
<212> TYPE: DNA
<213> ORGANISM: Artificial Sequence
<220> FEATURE:
<223> OTHER INFORMATION: synthetic

<400> SEQUENCE: 7
acccgttttt ttgggctaac aggaggaatt aaccatgggt aagaaacaga ccgctgttgc 60
attcgctctg gcgctcctgg ctctttctat gaccccggcg tacgct 106

<210> SEQ ID NO 8
<211> LENGTH: 106
<212> TYPE: DNA
<213> ORGANISM: Artificial Sequence
<220> FEATURE:
<223> OTHER INFORMATION: synthetic

<400> SEQUENCE: 8
acccgttttt ttgggctaac aggaggaatt aaccatgggt cgtaaacaga ccgcagtagc 60
attcgctctt gcgctgcttt ctctcgcttt caccaacgcg tacgct 106

<210> SEQ ID NO 9
<211> LENGTH: 74
<212> TYPE: DNA
<213> ORGANISM: Artificial Sequence
<220> FEATURE:
<223> OTHER INFORMATION: synthetic

<400> SEQUENCE: 9
ccatggctaa aaagaactcc accctgctcg ttgcagtagc tgcgctgatc ttcatggccg 60
gaagggccaa cgct 74

<210> SEQ ID NO 10
<211> LENGTH: 74
<212> TYPE: DNA
<213> ORGANISM: Artificial Sequence
<220> FEATURE:
<223> OTHER INFORMATION: synthetic

<400> SEQUENCE: 10
ccatggctaa aaagaactcc accctgctcg ttgcagtagc tgcgcttatc atgttcactc 60
agccggcgaa cgct 74

<210> SEQ ID NO 11
<211> LENGTH: 74
<212> TYPE: DNA
<213> ORGANISM: Artificial Sequence
<220> FEATURE:
<223> OTHER INFORMATION: synthetic

<400> SEQUENCE: 11
ccatgggtcg taaacagacc gctgttgcat tcgctctggc gctcctgtct cttgctttca 60
ccaacgcgta cgct 74

<210> SEQ ID NO 12
<211> LENGTH: 74
<212> TYPE: DNA
<213> ORGANISM: Artificial Sequence
<220> FEATURE:
<223> OTHER INFORMATION: synthetic

<400> SEQUENCE: 12
ccatgggtaa gaaacagacc gctgttgcat tcgctctggc gctcctggct ctttctatga 60
ccccggcgta cgct 74

-continued

<210> SEQ ID NO 13
<211> LENGTH: 74
<212> TYPE: DNA
<213> ORGANISM: Artificial Sequence
<220> FEATURE:
<223> OTHER INFORMATION: synthetic

<400> SEQUENCE: 13
ccatgggtaa gaaacagacc gctgttgcat tcgctctggc gctcctgtct cttgctttca 60
ccccggcgta cgct 74

<210> SEQ ID NO 14
<211> LENGTH: 24
<212> TYPE: PRT
<213> ORGANISM: Artificial Sequence
<220> FEATURE:
<223> OTHER INFORMATION: synthetic peptide

<400> SEQUENCE: 14

Met Gly Lys Lys Gln Thr Ala Val Ala Phe Ala Leu Ala Leu Leu Ser
1 5 10 15

Leu Ala Phe Thr Pro Ala Tyr Ala
20

<210> SEQ ID NO 15
<211> LENGTH: 74
<212> TYPE: DNA
<213> ORGANISM: Artificial Sequence
<220> FEATURE:
<223> OTHER INFORMATION: synthetic

<400> SEQUENCE: 15
ccatgggtcg taaacagacc gcagtagcat tcgctcttgc gctgctttct ctcgctttca 60
ccaacgcgta cgct 74

<210> SEQ ID NO 16
<211> LENGTH: 69
<212> TYPE: DNA
<213> ORGANISM: Escherichia coli

<400> SEQUENCE: 16
atgaaaaaga atatcgcatt tcttcttgca tctatgttcg ttttttctat tgctacaaac 60
gcgtacgct 69

<210> SEQ ID NO 17
<211> LENGTH: 23
<212> TYPE: PRT
<213> ORGANISM: Escherichia coli

<400> SEQUENCE: 17

Met Lys Lys Asn Ile Ala Phe Leu Leu Ala Ser Met Phe Val Phe Ser
1 5 10 15

Ile Ala Thr Asn Ala Tyr Ala
20

<210> SEQ ID NO 18
<211> LENGTH: 68
<212> TYPE: DNA
<213> ORGANISM: Erwinia carotovora

<400> SEQUENCE: 18
ccatgaaata cctgctgccg accgctgctg ctggtctgct gctcctcgct gcccagccgg 60

```
cgaacgct                                                            68


<210> SEQ ID NO 19
<211> LENGTH: 22
<212> TYPE: PRT
<213> ORGANISM: Erwinia carotovora

<400> SEQUENCE: 19

Met Lys Tyr Leu Leu Pro Thr Ala Ala Ala Gly Leu Leu Leu Leu Ala
1               5                   10                  15

Ala Gln Pro Ala Asn Ala
            20


<210> SEQ ID NO 20
<211> LENGTH: 65
<212> TYPE: DNA
<213> ORGANISM: Escherichia coli

<400> SEQUENCE: 20

ccatgaaaaa gacagctatc gcgattgcag tggcactggc tggtttcgct accgtagcgc     60

aggcc                                                                 65


<210> SEQ ID NO 21
<211> LENGTH: 21
<212> TYPE: PRT
<213> ORGANISM: Escherichia coli

<400> SEQUENCE: 21

Met Lys Lys Thr Ala Ile Ala Ile Ala Val Ala Leu Ala Gly Phe Ala
1               5                   10                  15

Thr Val Ala Gln Ala
            20


<210> SEQ ID NO 22
<211> LENGTH: 33
<212> TYPE: DNA
<213> ORGANISM: Artificial Sequence
<220> FEATURE:
<223> OTHER INFORMATION: synthetic

<400> SEQUENCE: 22

acccgttttt tgggctaaca ggaggaatta acc                                  33


<210> SEQ ID NO 23
<211> LENGTH: 24
<212> TYPE: PRT
<213> ORGANISM: Artificial Sequence
<220> FEATURE:
<223> OTHER INFORMATION: synthetic peptide

<400> SEQUENCE: 23

Met Ala Lys Lys Asn Ser Thr Leu Leu Val Ala Val Ala Ala Leu Ile
1               5                   10                  15

Phe Met Ala Gly Arg Ala Leu Ala
            20


<210> SEQ ID NO 24
<211> LENGTH: 72
<212> TYPE: DNA
<213> ORGANISM: Artificial Sequence
<220> FEATURE:
<223> OTHER INFORMATION: synthetic
```

-continued

```
<400> SEQUENCE: 24

atggctaaaa agaactccac cctgctcgtt gcagtagctg cgctgatctt catggccgga     60

agggccttgg cc                                                         72


<210> SEQ ID NO 25
<211> LENGTH: 16
<212> TYPE: DNA
<213> ORGANISM: Artificial Sequence
<220> FEATURE:
<223> OTHER INFORMATION: synthetic

<400> SEQUENCE: 25

taatgaattc aagctt                                                     16
```

LEADER PEPTIDES FOR ENHANCING SECRETION OF RECOMBINANT PROTEIN FROM A HOST CELL

CROSS REFERENCE TO RELATED APPLICATIONS

This application claims priority under 35 U.S.C. 119(e) to U.S. application Ser. No. 60/209,517, filed on Jun. 5, 2000, which application is incorporated by reference herein in its entirety.

INTRODUCTION

1. Technical Field

The invention relates to novel leader peptide sequences which are useful in a method for enhancing the secretion of recombinant proteins from a host cell, and nucleotide sequences encoding the leader peptides.

2. Background and Relevant Literature

Many commercially significant proteins are produced by recombinant gene expression in appropriate prokaryotic or eukaryotic host cells. It is frequently desirable to isolate the expressed protein product after secretion into the culture medium or, in the case of gram-negative bacteria, into the "periplasmic space" or "periplasm", between the inner and outer cell membranes. Secreted proteins are typically soluble and can be separated readily from contaminating host proteins and other cellular components. In many expression systems, the rate of secretion limits the overall yield of protein product and a considerable amount of product accumulates as an insoluble fraction inside the cell from where it is difficult to isolate. There is therefore a need to identify improved methods for directing the secretion of heterologous proteins from bacteria and other host-cell types.

The entry of almost all secreted proteins to the secretory pathway, in both prokaryotes and eukaryotes, is directed by specific signal peptides at the N-terminus of the polypeptide chain which are cleaved off during secretion. However, the mechanism by which signal peptides direct the nascent polypeptide chain to the secretion pathway and direct the precise and efficient proteolytic cleavage to release a mature protein are incompletely understood. Signal sequences are predominantly hydrophobic in nature, a feature which may be important in directing the nascent peptide to the membrane and transfer of secretory proteins across the inner membrane of prokaryotes or the endoplasmic reticulum membranes of eukaryotes. Secretion is, however, a multi-step process involving several elements of the cellular secretory apparatus and specific sequence elements in the signal peptide (see for example, Miller et al. (1998) J. Biol. Chem. 273: 11409–11412).

In mammalian cells, signal-sequences are recognized by the 54K protein of the signal recognition particle (SRP) which is believed to hold the nascent chain in a translocation-competent conformation until it contacts the endoplasmic reticulum membrane. The SRP consists of a 7S RNA and six different polypeptides. The 7S RNA and the 54K signal-sequence-binding protein (SRP54) of mammalian SRP exhibit strong sequence similarity to the 4.5S RNA and P48 protein (Ffh) of *Escherichia coli* which forms the signal recognition particle in bacteria (Luirink et al.(1992) Nature 359:741–743).

In addition to a hydrophobic stretch of amino acids that is characteristic of signal peptides, a number of common features are shared by the majority of secretion signals which function in prokaryotic cells and a distinct set of features are shared by signal peptides from eukaryotic cells.

In prokaryotic cells, many signal peptides are 20–30 amino acids in length, with the hydrophobic region (12–14 amino acid residues in length) in the middle, and a positively charged region close to the N-terminus (Pugsley (1993) Microbiol. Rev. 57:50–108). Despite the similarities, each signal peptide identified so far in *E. coli* has a unique sequence. It is likely that the various sequences found in different signal peptides interact in unique ways with the secretion apparatus.

A number of secretion signal peptides have been identified from prokaryotic proteins and from phage proteins (see, for example, Gennity et al. (1990) J. Bioeng. Biomemb. 22:233–269) which may be used to direct the secretion of heterologous recombinant proteins. Different signal peptides vary in the efficiency with which they direct secretion of heterologous protein but a limited number of prokaryotic signal peptides are now widely used for the secretion of heterologous proteins from *E. coli*, including the signal peptide from: Pectate lyase B protein from *Erwinia carotovora* (PelB); an *E. coli* outer membrane protein (OmpA; U.S. Pat. No. 4,757,013); heat-stable enterotoxin II (StII); alkaline phosphatase (PhoA), outer membrane porin (PhoE), and outer membrane lambda receptor (LamB). For example, the PelB signal peptide has been used to express antibody fragments from *E. coli* (U.S. Pat. No. 5,698,435).

In some cases, eukaryotic signal sequences may function in bacteria and vice versa (Zemel-Dreasen and Zamir (1984) Gene 27:315–322; Hall et al. (1990) J Biol Chem 265:19996–9; Garcia et al. (1987) J Biol Chem 262:9463–8).

Modifications of signal sequences have also been used to improve secretion levels. For example, a modified OmpA signal sequence has been used to secrete human NGF from *E. coli* (U.S. Pat. No. 5,470,719) and mutations in the hydrophobic core of the OmpA signal sequence enhanced the secretion of one bacterial protein (*Staphylococcus aureus* nuclease A) but not of a second bacterial protein (TEM beta-lactamase; Goldstein et al. (1990) J. Bacteriol. 172:1225–1231). A library of mutations in the LamB signal peptide identified improved leaders for secretion of bovine growth hormone (Klein et al. (1992) Prot. Eng. 5: 511–517).

Various attempts have been made to predict which N-terminal sequences may perform the function of a signal peptide. For example, a widely used algorithm is described in Nielsen et al. (1997) Prot. Eng. 10: 1–6. This algorithm predicts which sequences may serve as a signal peptide with a reasonable degree of accuracy. However, it does not predict which sequences will function most efficiently. Such methods are also only partially capable of predicting the sites of cleavage at the junction between the signal peptide and the mature protein; for example, the method of Nielsen et al. predicts correctly the site of cleavage of the signal peptide in only 89% of prokaryotic signal sequences. Indeed, signal peptidases, although biased towards regions containing a consensus sequence following the −3, −1 rule of von Heijne at the cleavage site, appear to recognize an unknown three-dimensional motif rather than a specific amino acid sequence around the cleavage site (Dev and Ray (1990) J Bioenerg Biomembr 22:271–90).

The choice of an appropriate signal sequence for the efficient secretion of a heterologous protein is made more difficult by the interaction of sequences within the cleaved signal peptide with downstream sequences within the mature protein. In prokaryotes there is a bias in the first 5 amino acids of a successfully cleaved mature protein for the amino acids Ala, Asp/Glu, Ser/Thr. Charged residues close to the N-terminus of the mature protein negatively influence secretion (the "charge block" effect) (Johansson et al. (1993) Mol Gen Genet. 239:251–256). Modulation of the effects of mutations in the basic region of the OmpA signal peptide by the mature portion of the protein have also been reported (Lenhardt et al. (1988) J. Biol. Chem. 263:10300–10303).

SUMMARY OF THE INVENTION

The present invention is directed to novel synthetic leader peptide sequences that are useful for enhancing the secretion of recombinant proteins produced in a variety of hosts and a method of designing the leader peptides. Also provided are polynucleotides comprising nucleotide sequences encoding the novel leader peptides and a method of designing the sequence of the polynucleotides. Another aspect of the invention is a method of enhancing the secretion of recombinant protein from a host by providing a fusion construct comprising nucleic acid encoding the novel leader peptide and the recombinant protein. Yet another aspect of the invention is a method of producing a recombinant protein by secreting the recombinant protein from a host cell through the use of the leader peptide. Also provided are expression vectors comprising the nucleic acid encoding the leader peptides or the fusion constructs. These and other aspects of the invention will be apparent from the disclosure provided herein.

DESCRIPTION OF SPECIFIC EMBODIMENTS

Definitions

Figure 1:
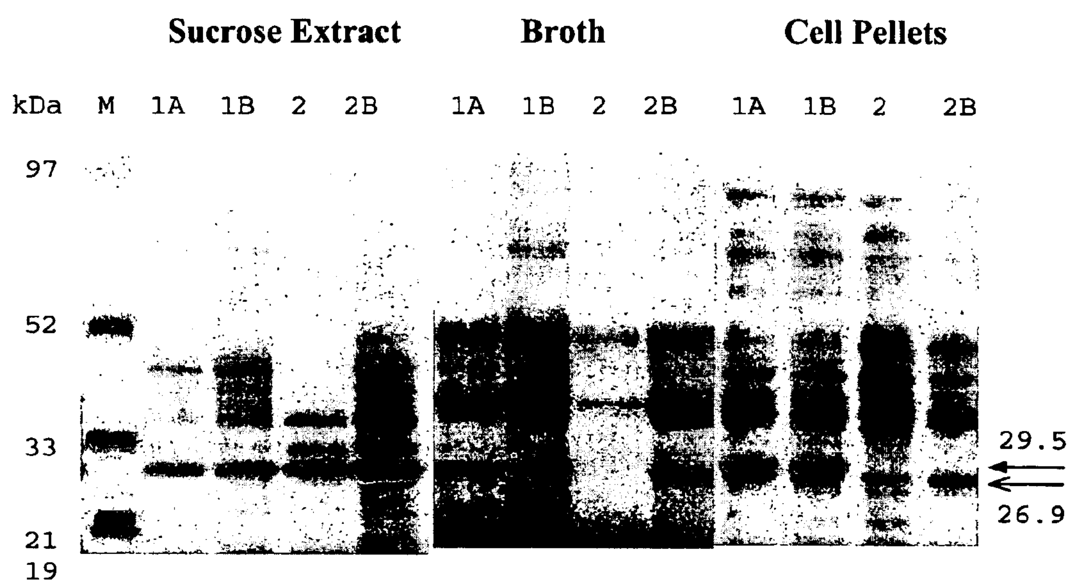
FIG. 1 shows stained polyacrylamide gels of protein samples from a sucrose extract, cell medium ("broth") and cell pellet. Ten milliliter cultures of bacterial strain TOP10 containing the leader peptide h4D5 scFv fusions were grown for four hours, induced with arabinose (0.01%), and harvested five hours after induction. Samples of 10, μl, 36 μl, and 5 μl were loaded of the sucrose extract, broth, and cell pellets, respectively. The molecular weights of the size markers (M) in kDa are shown on the left side of the gels, and the expected positions of the unprocessed 4D5 scFv and processed mature protein are shown by closed headed and open headed arrows, respectively, on the right side of the gels (expected molecular weight in kDa are also shown). The synthetic leader peptides used to secrete the scFv are labeled at the top of each lane where 1A, 1B, 2, and 2B correspond to the synthetic leader peptides SSS1A, SSS1B, SSS2, and SSS2B, respectively.

Generally, the nomenclature used herein, and the laboratory procedures in bacterial and animal cell culture, recombinant DNA and protein chemistry are those that are well known and commonly employed in the art. Unless otherwise defined, all technical and scientific terms used herein have the same meaning as commonly understood by one of ordinary skill in the art to which this invention belongs.

The amino acid sequence of the leader peptides of the invention is indicated in the usual manner for peptides or proteins, using the conventional one-letter or three-letter codes for the naturally occuring amino acids, and written with the amino terminus at the left and the carboxy terminus at the right, with adjacent amino acids being joined via normal amide, or "peptide" bonds.

Conventional notation is used when referring to nucleotide sequences herein. In general, only one strand of nucleotide sequence is shown even for double-stranded nucleic acids. When the nucleic acid encodes a protein, the coding strand is shown. The left-hand end of the nucleotide sequence is the 5' end, the right-hand end is the 3' end. Within the coding sequence, the 5'-most nucleotide sequence encodes the N-terminal amino acids, the 3'-most nucleotide sequence encodes the C-terminal amino acids. Nucleotide sequences that are 5' of the coding sequence are referred to as "upstream" and nucleotide sequences 3' of the coding sequence are referred to as "downstream."

By "leader peptide" is intended the peptide sequence present in a protein, generally at the N-terminus, which directs the protein into the secretory pathway. The leader peptide is cleaved from the protein during the secretion process by signal peptidases. The leader peptide may also be called the signal peptide, the leader sequence or the signal sequence.

By "recombinant protein" is intended a protein produced from a recombinant gene. By "recombinant gene" is intended a gene in a form other than its naturally occuring form as a result of some manipulation of the DNA or RNA in vitro. A naturally-occuring gene from one organism that is transferred into a heterologous organism, or into a homologous organism in a new genetic location, as a result of some manipulation in vitro is included as a "recombinant gene". The nucleotide sequence of the gene may or may not be modified during the process. A recombinant gene also includes a completely artificial gene, that is, one that does not occur naturally in any form. The term "gene" as used herein intends a nucleic acid coding for a protein and can include the entire coding region, with or without introns, and any regulatory sequences (e.g., promoter, enhancer, transcription start and stop) required for transcription and translation, or any portion thereof.

By "secretion" is intended the process by which a protein is transported into the external cellular environment or, in the case of gram-negative bacteria, into the periplasmic space.

By "fusion construct" is intended a nucleic acid comprising the coding sequence for a leader peptide and the coding sequence, with or without introns, for a recombinant protein, in which the coding sequences are adjacent and in the same reading frame such that, when the fusion construct is transcribed and translated in a host cell, a protein is produced in which the C-terminus of the leader peptide is joined to the N-terminus of the recombinant protein. The protein product of the fusion construct will be referred to herein as a "fusion polypeptide".

By "accessible" when applied to a ribosome binding site is intended that the bases of the ribosome binding site (RBS) in the mRNA are relatively available for binding of the ribosome. By "relatively available" is meant that no more than 70% of the bases of the RBS and the associated translational start codon are base paired in the model of mRNA secondary structure predicted using the Genequest program (DNASTAR, Inc., Madison, Wis.). The percentage of bases that are base paired can be calculated by dividing the number of bases that are base paired by the total number of bases in the ribosome binding site and the translational start codon multiplied by 100% [(number of bases of the RBS involved in base pairing+number of bases in the start codon involved in base pairing)/(number of bases of the RBS+number of bases in the start codon)×100%].

By "coding region" or "coding sequence" for a protein, polypeptide or peptide is intended the nucleotide sequence "encoding" the protein, polypeptide or peptide; that is, the nucleotide sequence (whether as DNA or RNA) containing the series of codons that are ultimately translated, or can be translated, by the appropriate cellular machinery, into the protein, polypeptide or peptide or portions of the same. The "coding region" need not contain the series of codons for the entire protein, polypeptide or peptide but may encode only a portion of the protein, polypeptide or peptide. The coding region may, but need not, contain introns that are spliced out to form a functional mRNA.

By "operatively joined" when referring to two or more macromolecules (polynucleotides, proteins, and the like) is meant that the component molecules or sequences are joined in such fashion that they function together to achieve the intended purpose. In referring to a ribosome binding site and a coding region, operatively joined means that the translation of the coding sequence is effected through ribosome binding at the ribosome binding site. In referring to two coding regions, operatively joined means that the coding regions are in frame and can be translated to produce a single polypeptide. In referring to a promoter and a gene or coding sequence, operatively joined means that the transcription of the gene or coding sequence is controlled by the promoter.

The present invention provides novel synthetic leader peptide sequences that are useful for enhancing the secretion of recombinant proteins from prokaryotic or eukaryotic hosts, and polynucleotides comprising the coding regions for the leader peptides. The leader peptides are typically between 20 and 25 amino acids in length, but may be as short as 15 or as long as 30 amino acids; that is, the leader peptidecan be 15, 16, 17, 18, 19, 20, 21, 22, 23, 24, 25, 26, 27, 28, 29 or 30 amino acid residues in length. The leader peptide is most effectively utilized by locating it at the N-terminus of a recombinant protein to be secreted from the host cell. Thus, the invention provides a fusion polypeptide comprising the leader peptide sequence and a recombinant protein sequence. Nucleic acid encoding the leader peptide can be operatively joined to nucleic acid containing the coding region of the recombinant protein in such manner that the leader peptide coding region is upstream of (that is, 5' of) and in the same reading frame with the recombinant protein coding region to provide a fusion construct. The fusion construct can be expressed in a host cell to provide a fusion polypeptide comprising the leader peptide joined, at its carboxy terminus, to the recombinant protein at its amino terminus. The fusion polypeptide can be secreted from the host cell. Typically, the leader peptide is cleaved from the fusion polypeptide during the secretion process, resulting in the accumulation of secreted recombinant protein in the external cellular environment or, in some cases, in the periplasmic space.

The amino acid sequence of the leader peptide of the invention may contain the following features: (1) two or more positively charged amino acids close to the N-terminus, (2) a region of between 7 and 16 consecutive hydrophobic amino acid residues, (3) one or more amino acids which acts as an alpha helix disrupter, and (4) at the C-terminus, the sequence Z-X-Z, wherein Z is an amino acid having a small side chain and X is any amino acid. Each of these features is described separately below. The leader peptide sequence will contain, at a minimum, features (1), (2) and (4) above. Preferably, the leader peptide will contain all four features above. The various features, when present, occur in the order presented above from the N-terminus to the C-terminus of the leader peptide, that is, the two or more positively charged amino acids close to the N-terminus are followed (in the direction of the C-terminus) by the region of hydrophobic amino acids, which is followed by the alpha helix disrupter(s), which is followed by the "Z-X-Z" sequence. In most embodiments, the "Z-X-Z" occurs immediately prior to the cleavage site for the leader peptide when that peptide is fused to a recombinant protein in a fusion polypeptide.

The leader peptide of the invention has two or more positively charged amino acid residues close to the N-terminus. By "close to the N-terminus" is meant that the positively charged amino acids residues occur within 2 to 6 amino acids of the N-terminus. In general, the positively charged amino acids do not occur at the N-terminus itself, as the N-terminus is typically a methionine residue or a formyl methionine residue. Nor do the positively charged amino acids occur directly adjacent to the N-terminal amino acid. Counting the N-terminal amino acid residue as 1, the positively charged amino acids will occur at two or more of residues 3, 4, 5, 6, or 7. The two or more positively charged amino acids are generally consecutive residues, but can be separated from one another by one or two intervening amino acids. Suitable intervening amino acids are those having small, uncharged side chains, for example, glycine, or alanine. Such intervening amino acids will preferably also separate the N-terminal amino acid from the two or more positively charged amino acids. The two or more positively charged amino acids can be the same amino acid or can be different. Suitable positively charged amino acids include lysine and arginine. Preferably there are two, three or four positively charged amino acids close to the N-terminus, more preferably there are two, three or four lysine residues close to the N-terminus.

The leader peptide of the invention has a region of between 7 and 16 consecutive hydrophobic amino acids; that is, the region may have 7, 8, 9, 10, 11, 12, 13, 14, 15, or 16 consecutive hydrophobic amino acids. Preferably, the hydrophobic region is between 12 and 16 amino acids in length. Suitable hydrophobic amino acids include alanine, leucine, valine, phenylalanine, threonine, isoleucine, serine, glutamine, asparagine, methionine, and tyrosine. The amino acid sequence for the region of hydrophobic amino acids can be randomly chosen from among the suitable hydrophobic residues but preferably is biased by ratios of A:L:V:F:T-:I:S:Q:N:M:Y of 16:14:14:5:5:4:3:2:2:1:1. Preferred hydrophobic amino acids are alanine, leucine, valine, phenylalanine, threonine, isoleucine, serine, glutamine, asparagine, and methionine; more preferred are alanine, leucine, valine, phenylalanine, threonine, serine, glutamine, methionine.

The leader peptide of the invention generally has at least one amino acid residue that acts as an alpha helix disrupter. In preferred embodiments, the alpha helix disrupter amino acid is located between the hydrophobic region and the Z-X-Z group at the leader peptide carboxy terminal. Preferably, there is one helix disrupter residue present, although there can be more than one up to about 10. Suitable amino acids that act as alpha helix disrupters include proline, arginine, glycine, lysine, glutamic acid, asparagine and aspartic acid. Preferably, a proline or an arginine residue is chosen as the helix disrupter; more preferably, a proline.

The leader peptide of the invention has, at the C-terminus, the sequence Z-X-Z, wherein "Z" is an amino acid having a small side chain and X is any of the twenty genetically encoded amino acids. By "C-terminus" when referring to the leader peptide is intended the end of the leader peptide sequence that is distal from the N-terminus. The C-terminus of the leader peptide can be joined to the N-terminus of the recombinant protein to form the secretable fusion polypeptide. Thus, it will be apparent that the C-terminus of the leader peptide is not an actual protein terminus when the leader peptide is joined to the recombinant protein. The "Z" amino acids can be the same or different from each other provided that each is an amino acid having a small side chain. Amino acids having a small side chain that are suitable as the "Z" in the "ZXZ" sequence include alanine, serine, glycine, valine or threonine. Preferably, at least one "Z" is an alanine residue. More preferably, both "Z" residues are alanines. Preferred "X" residues for the "ZXZ" sequence include tyrosine, asparagine and leucine.

A particularly preferred embodiment of the leader peptide of the invention has the following amino acid structure:

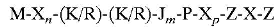

$$M\text{-}X_n\text{-}(K/R)\text{-}(K/R)\text{-}J_m\text{-}P\text{-}X_p\text{-}Z\text{-}X\text{-}Z$$

where each Z is independently an amino acid having a small side chain and each X is independently any genetically encoded amino acid, M, K, R and P are the conventional one-letter codes for methionine, lysine, arginine and proline respectively, (K/R) indicates that either a lysine or an arginine is in that position, each J is an amino acid independently selected from the group consisting of alanine, leucine, valine, phenylalanine, threonine, isoleucine, serine, glutamine, asparagine, methionine, and tyrosine, n is an integer selected from 1 or 2, p is an integer selected from 0, 1, or 2, and m is an integer selected from 7, 8, 9, 10, 11, 12, 13, 14, 15, or 16. In preferred embodiments, K/R is K, or n is 1, or p is 0, or m is 12, 13, 14, 15, or 16, or Z is alanine or X is alanine, glycine, tyrosine, or leucine, or combinations of the foregoing preferred selections.

Specifically preferred embodiments of the leader peptide include those having any of the following amino acid sequences:

MAKKNSTLLVAVAALIFMAGRANA (SEQ ID NO:1),
MAKKNSTLLVAVAALIMFTQPANA (SEQ ID NO:2)
MGKKQTAVAFALALLALSMTPAYA (SEQ ID NO:3)
MGRKQTAVAFALALLSLAFTNAYA (SEQ ID NO:4)
or
MAKKNSTLLVAVAALIFMAGRALA (SEQ ID NO:23),

In addition to amino acid sequence considerations, efficient secretion of a fusion polypeptide requires attention to the nucleic acid environment, particularly at the mRNA level, of the coding region for the fusion polypeptide. Therefore, the invention also provides polynucleotides comprising nucleic acid sequences encoding the leader peptides and including the nucleic acid sequences upstream of the translational start site (that is, 5' of the translational start on the coding strand). The polynucleotide of the invention comprises a first nucleotide sequence encoding a leader peptide, wherein said leader peptide comprises (1) two or more positively charged amino acids close to the N-terminus, (2) a region of between 7 and 16 consecutive hydrophobic amino acid residues, (3) optionally, an amino acid which acts as an alpha helix disrupter, and (4) at the C-terminus, the sequence Z-X-Z, wherein each Z is independently an amino acid having a small side chain and X is any genetically encoded amino acid, and a second nucleotide sequence comprising a ribosome binding site, wherein said second nucleotide sequence is 5' of said first nucleotide sequence and the ribosome binding site is operatively joined to the coding region for the leader peptide, and wherein, when said polynucleotide is RNA or is transcribed into RNA, said ribosome binding site is accessible, as defined herein.

The choice of appropriate nucleotide sequence for the polynucleotide begins with a determination of all possible nucleotide sequences that can encode the amino acid sequence of the leader peptide with reference to the genetic code, as is well known in the art. In designing the nucleotide sequences for the polynucleotide of the invention, consideration will be given to the codon bias of the intended host organism and the potential for secondary structure in the RNA.

With regard to the codon bias considerations, in general, the polynucleotide sequence is designed using the codon bias for the host organism in which the leader peptide/fusion polypeptide will be expressed; that is, the codon usage chosen for the nucleic acid sequences encoding the leader peptide will reflect, as closely as practical, the codon usage in the intended host organism. The codon bias for a number of prokaryotic and eukaryotic organisms is well known. See, for example, Sharp and Matassi (1994) Curr. Opinion Genet. Devel. 4:851–860; Zhang and Zubay (1991) Genetic Engineering 13:73–113.

In addition to considerations relating to the codon bias, the secondary structure of the mRNA encoding the leader peptide can influence translation and it may be desirable to optimize the sequence of the RNA in this region to obtain efficient secretion of the encoded protein. "Silent" mutations (mutations which do not alter the peptide sequence) introduced into the DNA coding for signal peptides have been shown to influence the efficiency of expression of antibody Fv fragments in *E. coli* (Stemmer et al. (1993) Gene 123: 1–7). Optimization of expression, in this regard, does not necessarily require selection of the maximal possible rate of translation. Rather, a reduced translation rate may permit improved protein folding and thereby enhance the overall secretion rate.

In particular, with regard to the secondary structure considerations, the nucleic acid sequence encoding the leader peptide and the nucleic acid sequence immediately upstream of the coding sequence are designed to optimize the availability of the ribosome binding site of the mRNA produced. The availability of the ribosome binding site (RBS) can be predicted from the secondary structure of nucleic acid of the mRNA surrounding the RBS by methods that are well known in the art. For example, the secondary structure of the mRNA can be determined using the Genequest program available from DNASTAR, Inc. (Madison, Wis.). The Genequest program uses the Vienna modifications (Schuster et al. Proc. R. Soc. Lond. B. Biol. Sci. (1994) 255:279–284) of the optimal RNA folding method described by Zuker (Zuker, M. Science (1989) 244:48–52 and Jaeger et al. Proc. Natl Acad. Sci. USA (1989) 86:7706–7710) to predict RNA secondary structure. By applying such a method to a nucleotide sequence containing the RBS and the coding sequence for the leader peptide, it is possible to determine the availability of the RBS to ribosome binding. In general, the availability of a ribosome binding site can be described in terms of the number of bases within the RBS itself and within the AUG translational start codon that are involved in base pairing in the RNA secondary structure and whether the RBS and AUG are buried in the stem of a stem-loop structure. In general, the fewer bases of the RBS and AUG that are involved in base pairing, the more available the RBS is to ribosome binding. Similarly, the RBS is more available to ribosome binding when it is not buried within a stem-loop structure. Typically, the analysis of the mRNA secondary structure will consider the sequence of the mRNA from the beginning (that is, the 5' end of the mRNA) through the ribosome binding site and the translational start (AUG) up to the end of the leader peptide coding region. The sequence of the mRNA upstream of the AUG will usually depend upon the sequence of the particular promoter used in making the fusion construct. Thus, the secondary structure of the mRNA will be influenced not only by the choice of amino acid sequence for the leader peptide but also by choice of promoter and RBS used.

When the Genequest program is used for RNA secondary structure determinations, the temperature parameter will be set at 37° C. and GU pairing will be permitted. The output of the Genequest program is a graphic display of the structure of the RNA showing the predicted base-paired regions. The preferred nucleotide sequence for a leader peptide having a particular amino acid sequence will be one having no more than 70% of the bases of the RBS and the associated AUG translational start codon involved in secondary structure (i.e., base-pairing) and will have a RBS that is not buried within a stem-loop structure. In calculating the percentage of bases involved in base-pairing, the number of bases of the RBS and the AUG involved in base-pairing will be combined and compared to the total number of bases in the RBS and AUG combined. In determining the RNA secondary structure, the sequence of the polynucleotide from the promoter through the end of the coding region for the leader peptide will be considered.

In bacterial systems, a ribosome binding site typically has a sequence complementary to the 3' end of 16s rRNA (see, for example, Ringquist, S. et al. (1992) Mol. Microbiol. 6:1219). A useful ribosome binding site for use in connection with the present invention is one naturally associated with the AraBAD promoter from *E. coli*. This promoter can be conveniently found in pBAD-HisA vector (Invitrogen). This particular ribosome binding site has the nucleotide sequence AGGAGG.

The polynucleotide of the invention can be RNA or DNA and can be single-stranded or double-stranded. When the polynucleotide is RNA, the determination of secondary structure will be carried out using the nucleotide sequence of the polynucleotide. When the polynucleotide is DNA, the determination of secondary structure will be carried out using the nucleotide sequence of the corresponding RNA. By "corresponding RNA" is intended an RNA having the same nucleotide sequence as the DNA polynucleotide except for the replacement of T with U.

Thus, it will be apparent that a method for designing a polynucleotide encoding a fusion polypeptide for enhanced secretion of the fusion polypeptide must include consideration of the amino acid sequence of the leader peptide and the nucleotide sequence encoding the leader peptide and the region upstream from the leader coding sequence in the mRNA. The method of the present invention for designing a polynucleotide encoding a fusion polypeptide for enhanced secretion of the fusion polypeptide comprises: (a) selecting a first nucleotide sequence encoding a leader peptide, wherein said leader peptide comprises (1) two or more positively charged amino acids close to the N-terminus, (2) a region of between 7 and 16 consecutive hydrophobic amino acid residues, (3) optionally, an amino acid which acts as an alpha helix disrupter, and (4) at the C-terminus, the sequence Z-X-Z, wherein each Z is independently an amino acid having a small side chain and X is any amino acid;

(b) selecting a second nucleotide sequence comprising a ribosome binding site, wherein when said second nucleotide sequence is operatively joined to said first nucleotide sequence such that said second nucleotide sequence is 5' of said first nucleotide sequence, and when said joined first and second nucleotide sequence is RNA or is transcribed into RNA, said ribosome binding site is accessible; (c) selecting a third nucleotide sequence encoding a recombinant protein, wherein said third nucleotide sequence is 3' of and operatively joined to said first nucleotide sequence in such manner that a fusion polypeptide comprising said leader peptide and said recombinant protein is encoded; and (d) assembling the first, second, and third nucleotides sequences into a single polynucleotide. The assembling of the various nucleotide sequences will be accomplished by any of a number of techniques that are well known in the art, for example, by ligation of restriction fragments or PCR generated fragments, by PCR amplification or by synthesis of the entire polynucleotide or portions thereof.

Preferred polynucleotides of the invention will have one of the following nucleotide sequences:

5'ACCCGTTTTTTTGGGCTAACAGGAGGAATT-AACCATGGCTAAAAAGAACTCCACCCTGCTCGTT-GCAGTAGCTGCGCTGATCTTCATGGCCGGAAGGG-CCAACGCT3' (SEQ ID NO:5)

5'ACCCGTTTTTTTGGGCTAACAGGAGGAATTAA-CCATGGCTAAAAAGAACTCCACCCTGCTCGTTGCA-GTAGCTGCGCTTATCATGTTCACTCAGCCGGCGAA-CGCT3' (SEQ ID NO:6)

5'ACCCGTTTTTTTGGGCTAACAGGAGGAATTAA-CCATGGGTAAGAAACAGACCGCTGTTGCATTCGCT-

CTGGCGCTCCTGGCTCTTTCTATGACCCCGGCGTACGCT3' (SEQ ID NO:7) or

5'ACCCGTTTTTTTGGGCTAACAGGAGGAATTAACCATGGGTCGTAAACAGACCGCAGTAGCATTCGCTCTTGCGCTGCTTTCTCTCGCTTTCACCAACGCGTACGCT3' (SEQ ID NO:8).

The translational start codon for the leader peptide is italicized in each of the foregoing sequences.

Recombinant proteins, and the nucleotide sequences encoding the same, that are useful in connection with the leader peptides of the invention include bacterial proteins and eukaryotic proteins such as mammalian proteins, or more preferably human proteins. Examples of human recombinant proteins are natural human proteins such as insulin, human growth hormone, interferons, and proteins of the immunoglobulin superfamily, including immunoglobulins and MHC proteins; and mutant versions of human proteins such as consensus interferon or protein fragments such as immunoglobulin fragments such as Fab or Fv fragments. Alternatively, the recombinant protein can be a non-naturally occurring or engineered protein such as a variant of a natural human protein, a fragment of a natural protein, a chimeric protein or an entirely novel engineered protein. The recombinant protein may be one that naturally occurs or functions as a monomer or may be one or more polypeptide subunits of a larger polypeptide complex, for example, a homodimer, or heterodimer or other multimeric protein. The multimeric protein may be composed of identical polypeptide subunits or may be composed of a number of non-identical polypeptide subunits. Examples of recombinant proteins useful in the present invention include immunoadhesins (for example, CTLA4-Ig), and proteins containing immunoglobulin-derived variable domains including scFvs, Fab and F(ab')2 fragments of antibodies, single chain antibodies, bispecific antibodies, diabodies. The immunoglobulin variable domains and antibody fragments may be human or humanised and may be joined to human or mouse constant domains. If the recombinant protein is a multimeric protein, then the coding region for each polypeptide subunit making up the multimer may be linked to a leader peptide at its N-terminus. The leader peptides chosen may be the same or different for each of the polypeptide subunits. In the case where the recombinant protein is a naturally secreted protein, typically the coding sequence for only the mature form of the protein is used in the fusion construct, with the synthetic leader peptide of the invention replacing the naturally occurring leader peptide.

In one aspect of the invention, the synthetic leader peptide is used to direct or enhance the secretion of the recombinant protein produced in a recombinant (i.e., transformed) host organism. In a preferred embodiment, the synthetic leader peptide is used to direct or enhance the secretion of an immunoglobulin related polypeptide, such as a recombinant protein having as its N-terminal domain, an immunoglobulin variable domain. Such variable domains include Vh domains and Vl domains from heavy or light chains of antibodies, respectively. These domains may be part of larger recombinant proteins such as scFvs, Fab and F(ab')2 fragments of antibodies, single chain antibodies, bispecific antibodies or diabodies. Since the N-terminal residues of the mature recombinant protein can affect the cleavage of the leader peptide, secretion levels may be further optimised by appropriate choice of amino acid residues in the vicinity of the leader peptide cleavage site. For example, charged residues in the region of the N-terminus of the recombinant protein should be avoided if possible. In addition, placement of a proline residue at either side of the cleavage site should be avoided. In a more preferred embodiment, the synthetic leader peptide is used to direct or enhance the secretion of an immunoglobulin related polypeptide from a procaryotic host.

The polynucleotides of the present invention are prepared by any of a variety of methods that are well known in the art and described, e.g.,in Sambrook, J. Fritsch, E. F., and Maniatis, T. (1989) Molecular Cloning: A Laboratory Manual, Cold Spring Harbor Laboratory Press, Cold Spring Harbor, N.Y. or Ausubel et al. (1998) Current Protocols in Molecular Biology, John Wiley & Sons, Inc. Nucleic acids may be readily synthesized by use of an automated DNA synthesizer (such as are commercially available from Biosearch, Applied Biosystems, etc.). Discrete fragments of DNA (for instance, DNA encoding the recombinant protein) can be prepared and cloned using restriction enzymes. Alternatively, discrete fragments can be prepared using the Polymerase Chain Reaction (PCR) using primers having an appropriate sequence.

The polynucleotides encoding the leader peptide of the invention can be joined to nucleic acid encoding a recombinant protein to provide a fusion construct. Typically, the 3' end of the nucleic acid encoding the leader peptide is joined to the 5' end of the nucleic acid encoding the recombinant protein. The two coding regions are joined such that they are in the same reading frame. In this way, the fusion construct will encode a single protein, having the leader peptide at the N-terminal end followed by the recombinant protein at the C-terminal end. The leader peptide and the recombinant protein may be joined directly or there may be one or several amino acids connecting them. Certain amino acids are well known to interfere with designing the cleavage site for the fusion polypeptide. If the recombinant protein normally (that is, in the native form) contains a signal sequence, this sequence is preferably not included in the fusion polypeptide. Likewise, if the recombinant protein normally contains an initial Met (or formyl-Met) residue at the N-terminus, this Met (or formyl-Met) is typically not included in the fusion polypeptide.

Expression vectors can be prepared containing the nucleic acids encoding the leader peptide or the fusion construct by methods that are well known in the art. In general, the expression vectors will contain nucleic acid encoding the leader peptide, or the fusion construct, under the control of a promoter. In some embodiments, more than one leader peptide or fusion construct will be placed under the control of a single promoter. In such embodiments, a di-cistronic or polycistronic message can be produced by transcription from the single promoter. In these embodiments, the additional fusion construct(s) will be placed downstream of the first fusion construct and separated from the upstream fusion construct by no more than 30 nucleotides; that is, there will be no more than 30 nucleotides separating the stop codon of the upstream fusion construct from the translational start codon of the downstream fusion construct. Preferably, the fusion constructs in a di-cistronic or polycistronic embodiment will be separated by between 1 and 30 nucleotides, more preferably by between 3 and 20 nucleotides. In some cases the fusion constructs may even be slightly overlapping.

The promoter is chosen so that it is capable of directing transcription in a host of interest. Promoters capable of directing transcription in various host cells are well known and some examples are described below. Any suitable promoter may be chosen. In general, a "promoter" will include all nucleotide sequences upstream of the translational start (the AUG codon) necessary for the transcription of the leader peptide or fusion polypeptide coding region. The promoter may include or overlap the sequence of the ribosome binding site. Selection of promoter will often influence the selection of ribosome binding site as well. As described elsewhere herein, the particular nucleotide sequence of the promoter will influence the selection of leader peptide coding region with which it is paired. The expression vector may also contain a selectable marker gene for selection in the host of interest and/or an origin of replication to provide autonomous replication of the vector in the host. Alternatively, or in addition, the expression vector may contain nucleotide sequences to aid in integration of the vector into the host chromosome.

Methods to construct expression vectors for production of fusion polypeptide in various hosts are also generally known in the art. Expression can be effected in either prokaryotic or eukaryotic hosts. Prokaryotes most frequently are represented by various strains of *E. coli*. However, other microbial strains may also be used, such as bacilli, for example *Bacillus subtilis*, various species of Pseudomonas, or other bacterial strains. In such prokaryotic systems, plasmid vectors which contain replication sites and control sequences derived from a species compatible with the host are often used. For example, workhorse vectors for *E. coli* include pBR322, pUC18, pBAD and their derivatives. Commonly used prokaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, the arabinose promoter, and the lambda-derived $P_L$ promoter and N-gene ribosome binding site. However, any available promoter system compatible with prokaryotes can be used. Techniques useful for the production of recombinant proteins in *E. coli* are found in Baneyx, F. (1999) Curr. Opinion Biotech. 10:411–421, and U.S. Pat. No. 5,698,435.

Expression vectors useful in eukaryotic hosts comprise promoters derived from appropriate eukaryotic genes. A class of promoters useful in yeast, for example, includes promoters for synthesis of glycolytic enzymes, e.g., those for 3-phosphoglycerate kinase. Other yeast promoters include those from the enolase gene or the Leu2 gene obtained from YEp13. Suitable promoters for mammalian cells include the early and late promoters from SV40 or other viral promoters such as those derived from polyoma, adenovirus II, bovine papilloma virus or avian sarcoma viruses, human cytomegalovirus (hCMV) promoters, such as the hCMV-MIE promoter-enhancer. Additional suitable mammalian promoters include the β-actin promoter-enhancer and the human metallothionein II promoter. In the event plant cells are used as a host for the expression vector, the nopaline synthesis promoter from *A. tumefaciens*, for example, is appropriate.

The expression vectors are constructed using well-known techniques, for example, restriction and ligation techniques, homologous recombination techniques or PCR amplification techniques, and transformed into appropriate hosts. Transformation of host cells is accomplished using standard techniques suitable to the chosen host cells. The cells containing the expression vectors are cultured under conditions appropriate for production of the fusion polypeptide, and the fusion polypeptide or the cleaved mature recombinant protein (that is, the expressed protein with or without the leader peptide) is then recovered and purified. In general, the protein that will be recovered is the fusion polypeptide or the recombinant protein (after cleavage of the leader peptide), or both. It will be apparent that when the fusion polypeptide is secreted and the leader peptide is cleaved during the process, the protein that will be recovered will be the recombinant protein, or a modified form thereof. In some cases, the fusion polypeptide will be designed such that there are additional amino acids present between the leader peptide and the recombinant protein. In these instances, cleavage of the leader peptide from the fusion polypeptide may produce a modified recombinant protein having additional amino acids at the N-terminus. Alternatively, the fusion polypeptide may be designed such that the site for cleavage of the leader peptide occurs a few amino acids into the sequence of the recombinant protein. In these instances, a modified recombinant protein may be produced which has an altered N-terminus.

Nucleic acids encoding the leader peptide of the present invention, including the fusion constructs and the expression vectors, can be transformed into a host cell of interest by methods that are appropriate for the host chosen and are well known in the art and described in Ausubel et al. (1998), supra.

The present invention also provides a method for producing a recombinant protein in a host cell comprising transforming a host cell with an expression vector comprising the fusion construct, wherein the expression vector also comprises a promoter that is functional in the chosen host cell, and culturing the transformed host cell under conditions such that the fusion polypeptide is expressed and secreted from the host cell. The host cell may be a prokaryotic cell, for example, *E.coli*, or a eukaryotic cell, for example, a fungal cell (e.g., a yeast cell), an insect cell, a plant cell or a mammalian cell. Mammalian cells suitable for use in this aspect of the invention include cells of transgenic animals and tissue culture cells. Preferably, the mammalian host cell is an established cell line such as a Chinese hamster ovary (CHO) cell, a rodent myeloma or hybridoma cell line or a human cell line. For each particular host, the expression vector will be chosen such that the promoter and the selectable marker, if present, are functional in the chosen host. In addition, the nucleotide sequence encoding the leader peptide can be optimized for the particular host as described herein. The transformed host cells are cultured under conditions appropriate for expression of the fusion polypeptide encoded by the expression vector. The appropriate conditions will vary with the particular host chosen and the particular promoter controlling expression of the fusion polypeptide. One of ordinary skill in the art is competent to select appropriate culturing conditions. The production of the fusion polypeptide and/or the recombinant protein can be monitored in any of a number of ways that will be apparent to those skilled in the art. For example, protein levels in the cytoplasm, periplasm or culture medium can be monitored by enzymatic assay or by densitometry of bands on protein stained PAGE gels.

The following examples are provided by way of illustration of the invention and are not intended to be limiting.

EXAMPLES

Example 1

Design of Leader Peptides and Preparation of Fusion Constructs with h4D5scFv The amino acid sequences for three leader peptides were designed for fusion at the N-terminus of a recombinant protein. The three amino acid sequences initially chosen are shown below as SSS1A, SSS1B and SSS2.

Nucleotide sequences encoding the synthetic protein sequences were constructed by standard oligonucleotide synthesis techniques and inserted into the plasmid pBAD/HisA (Invitrogen). The nucleotide sequences chosen to encode each of the leader peptides are shown below. The synthetic leader peptides were compared to known leader peptides, the StII, OmpA and the pelB leader sequences, for the ability to direct the secretion of a protein (the pelB leader was slightly modified from the known sequence). DNA encoding the synthetic leader peptide sequences or the naturally occurring signal sequences were each joined to the 5'-end of a DNA sequence encoding h4D5scFv (Carter et al. 1992, Proc. Natl. Acad. Sci., USA, 89, 4285–4289) in pBAD/HisA plasmid (Invitrogen) and the expression plasmids were introduced into *E. coli* for evaluation of h4D5scFv expression after arabinose induction according to the manufacturer's instructions.

The 4D5 scFv gene with the StII leader peptide and a C-terminal hexa-histidine tag was constructed by PCR using synthetic oligonucleotides, and then cloned as a BspHI-HindIII fragment into the pBAD/HisA vector, pre-digested with NcoI and HindIII. Additional constructs were prepared from other naturally occuring or synthetic leader peptides by introducing synthetic oligonucleotide cassettes encoding the leader peptides as NcoI-SacI, NcoI-BsiWI, or NcoI-NgoMIV fragments. The DNA sequence of the leader peptides constructs was verified by DNA sequencing. *Escherichia coli* strain TOP10 was transformed with the pBAD based expression vectors for monitoring protein production.

Example 2

Preparation of the Fusion Polypeptide

Bacterial colonies for each of the transformants from Example 1 were picked and grown overnight in 3 ml of SuperBroth with 100 μg/ml of carbenicillin. This pre-culture (100 μl) was used to inoculate 10 ml of SuperBroth with 100 μg/ml of carbenicillin in a 50 ml conical tube. The cultures were grown to mid-log phase (3.75–4 h), induced with 0.01% arabinose, and harvested after 4.5–5 h. Cultures were grown at 30° C. with shaking at 150 rpm. Cells were harvested by centrifugation for ten minutes at 10,000 rpm in an SL-250T rotor (Sorvall). Proteins in the samples of the broth supernatants were precipitated with TCA. The cell pellets were resuspended in 2.5 ml of ice cold sucrose buffer (20 mM Tris-HCl pH 8.0, 28% sucrose, and 2 mM EDTA), placed on ice for ten minutes, and then centrifuged for 15 minutes at 14,000 rpm in an SL-250T rotor (Sorvall). Proteins in the sucrose extract were precipitated with TCA and a small sample of cell pellet was taken up in NuPAGE sample buffer (Novex) for PAGE analysis. TCA precipitates were collected by centrifugation, washed with cold (−20 ° C.) acetone, the pellets dried using a SpeedVac (Savant), and resuspended in 200 μl of NuPAGE sample buffer. All protein samples were heated for 10 minutes at 100 ° C. before loading on a 4–12% NuPAGE gel (Novex) and the gel was run in MOPS buffer (Novex) at 200 volts. After electrophoresis, the gels were washed 3 times in about 50 ml of deionized water for 5 minutes each. The gels were then stained for one hour in GELCODE Blue Stain Reagent (Pierce) and destained for several hours in several changes of deionized water. Dried gels (DryEase—Novex) were scanned (Fotolook software—AGFA) using a flat bed scanner (Duoscan T1200 —AGFA) with a yellow filter for contrast. The 4D5 scFv protein band intensity was determined using Slot-Blot Analysis software (GelExpert—Nucleotech) and graphed as intensity per unit area. Background was taken from the equivalent molecular weight region in the marker lane and subtracted from the intensity values. The correct 4D5 scFv band was verified by positive signals on blots probed with either INDIA HisProbe-HRP (Pierce) or by ImmunoPure Protein L-peroxidase conjugated reagent (Pierce).

Each of the synthetic leader peptides was capable of acting as a secretion signal as determined by the appearance of mature h4D5 scFv protein in the culture broth, analysed by polyacrylamide gel electrophoresis (PAGE) according to standard techniques. The identity of the scFv protein band was confirmed by Western blotting using peroxidase-conjugated Protein-L. In an initial experiment, surprising differences in the efficiency of the three synthetic signal sequences were observed. SSS1A generated a similar amount of h4D5 scFv secreted into the culture broth to that secreted using the StII prokaryotic signal sequence. SSS1B produced more secreted h4D5 scFv than either the StII or SSS1A and SSS2 produced the smallest amount of secreted scFv.

In an attempt to define which elements contribute to the differences in secretion efficiency, the SSS2 leader peptide was further modified to form SSS2B. In SSS2B, the amino acid sequence RK near the N-terminus was changed to KK as in the SSS1 leader peptides, an alanine was moved closer to the center of the hydrophobic core, and the asparagine residue was replaced with a proline as the (α-helix breaker adjacent to the AXA. The secretion of h4D5 scFv was then tested using the SSS2B as a signal sequence and compared to two commonly used prokaryotic signal sequences, OmpA and PelB*. PelB* is a modified form of the pectate lyase (PelB) signal sequence in which the sequence QPAMA at the C-terminal was replaced with QPANA. The production of the scFv extracted from the periplasm, or present in the culture medium, was significantly increased by using SSS2B as a leader peptide when compared to SSS2. Amounts of scFv in the periplasm produced using SSS2B were also higher than that produced using either the OmpA or PelB* signal sequences. Levels of scFv accumulated in the culture medium using SSS2B as the leader peptide were similar to the levels obtained with OmpA and much greater than using the PelB* signal sequence.

Figure 2:
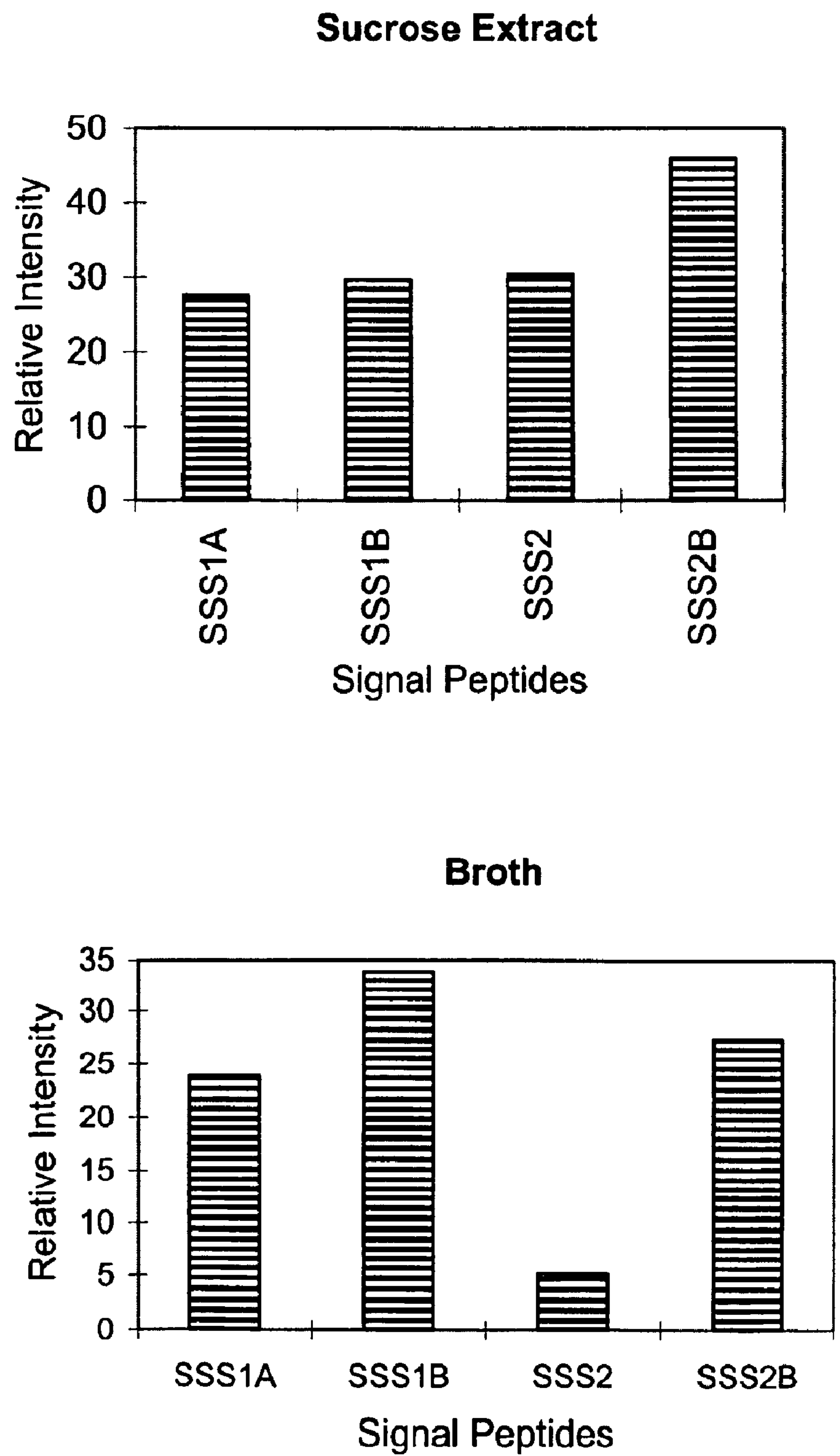
FIG. 2 shows bar graphs of the relative intensity of the stained h4D5scFv bands from the gels in FIG. 1.
Figure 3:
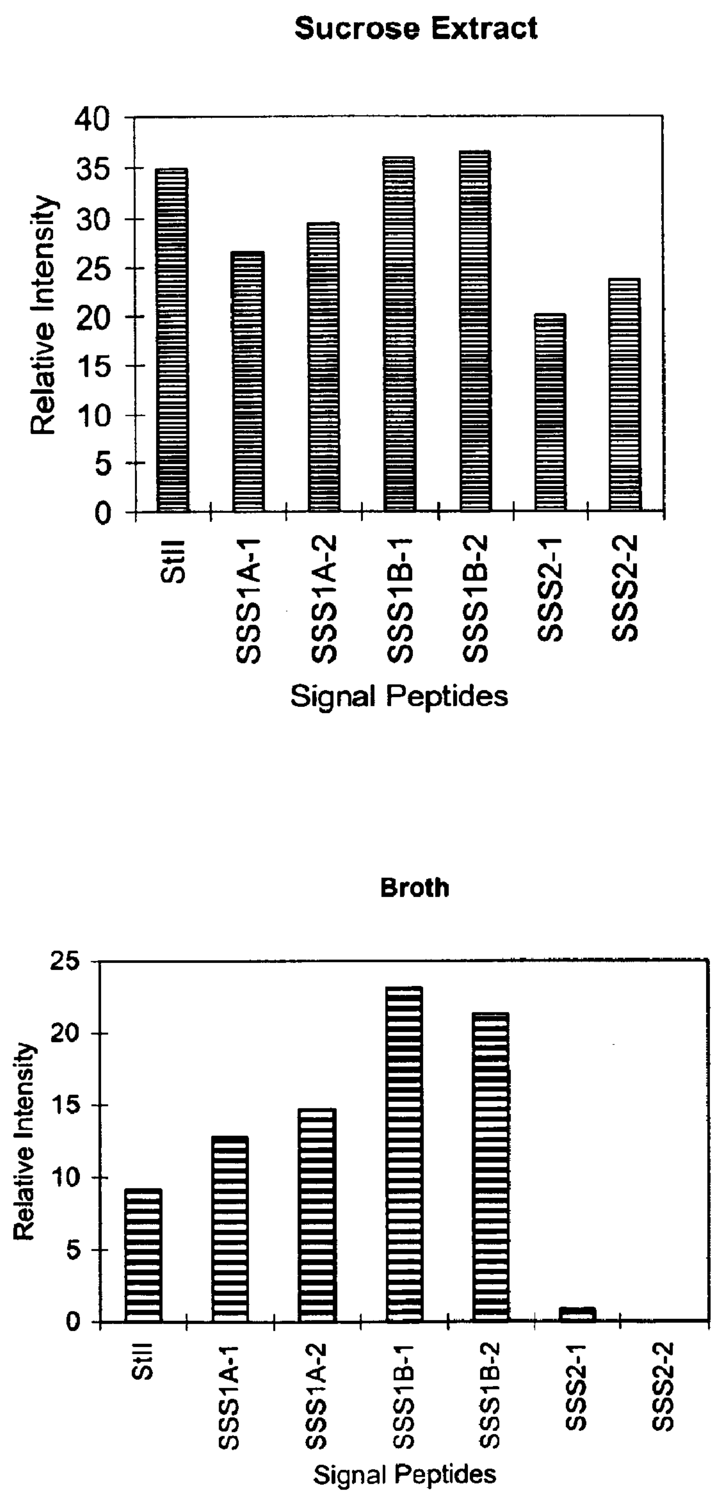
FIG. 3 shows bar graphs of the relative intensity of stained h4D5scFv bands after PAGE of protein samples obtained from bacteria transformed with various leader peptide-h4D5scFv fusions, including fusions with the naturally occurring StII leader peptide. Protein samples obtained from the sucrose extract and culture medium ("broth") are shown in separate graphs. Ten milliliter cultures of TOP10 transformed with the fusion constructs were grown for 3.75 hours, induced with arabinose (0.01%), and harvested 4.5 hours after induction. Samples of 10 μl and 34 μl were loaded of the TCA precipitated sucrose extracts and broth samples, respectively. Two different clones of SSS1A, SSS1B, and SSS2 (labeled 1 and 2) were analyzed from the stained protein gels.
Figure 4:
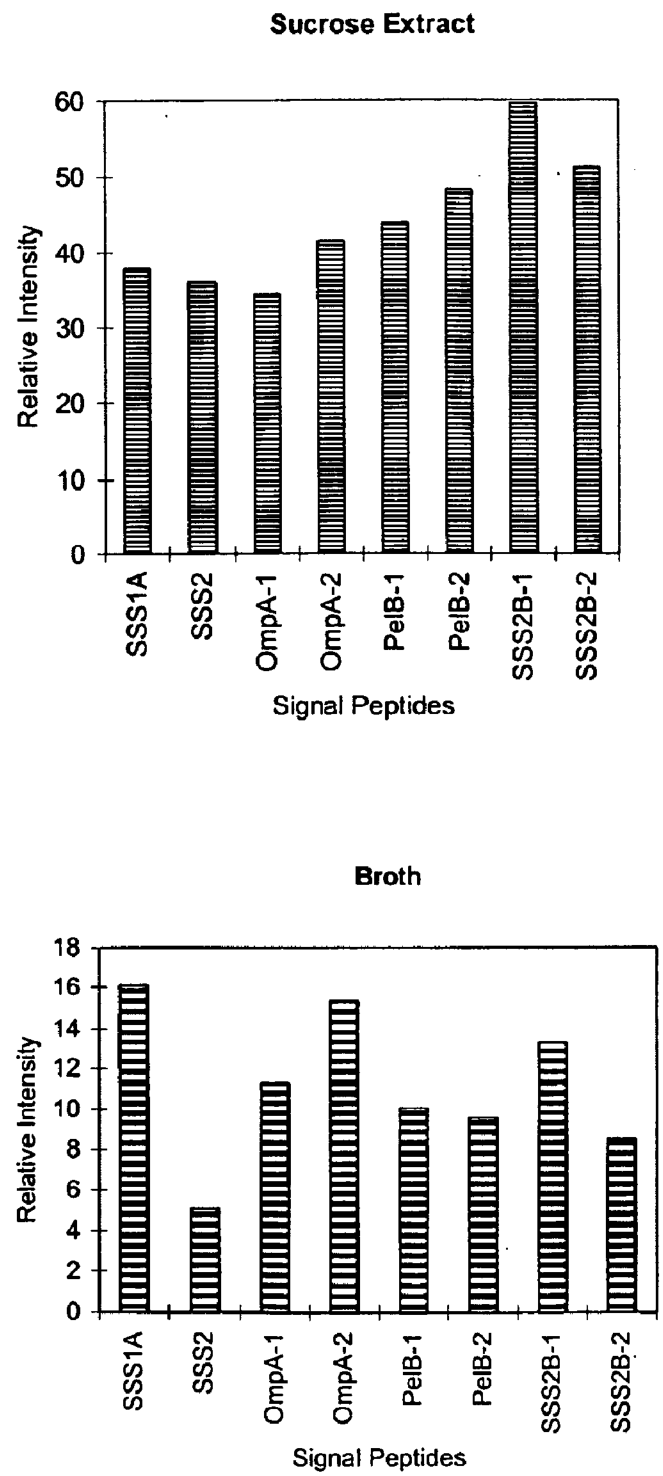
FIG. 4 shows bar graphs of the relative intensity of stained h4D5scFv bands after PAGE of protein samples obtained from bacteria transformed with various leader peptide-h4D5scFv fusions, including fusions with the naturally occurring OmpA and PelB leader peptides. Protein samples obtained from the sucrose extract and culture medium ("broth") are shown in separate graphs. Ten milliliter cultures were grown for 4 hours, induced with arabinose (0.01%), and harvested 5 hours after induction. Samples of 10 μl and 34 μl were loaded of the TCA precipitated sucrose extracts and broth samples, respectively. Two different clones of OmpA, PelB and SSS2B (1 and 2) were tested.

Representative gels for the production of the 4D5 scFv in sucrose extracts, broth, or cell pellets when fused to four different synthetic leader peptides are shown in FIG. 1. To assess the efficiency of the leader peptides to drive the secretion of the 4D5 scFv protein, the intensity of the stained bands was determined and plotted in a bar graph (FIG. 2). As can be seen in FIGS. 1 and 2, SSS2 does not produce as much protein in the broth samples as the other three synthetic leader peptides. This is most likely due to poor (or delayed) secretion into the periplasm which results in less subsequent leakage of protein into the culture broth. In fact, at earlier time points, or lower arabinose induction concentrations, there is consistently less 4D5 scFv produced in the sucrose extract with the SSS2 fusion construct than with the fusion constructs made using the other synthetic leader peptides (data not shown). With the exception of SSS2, the synthetic leader peptides SSS1A, SSS1B, and SSS2B, produce equivalent amounts of the 4D5 scFV protein as the commonly used leader peptides StII, PelB, and OmpA (see FIGS. 3 and 4). In fact, under the conditions tested, SSS2B typically produces about 10% more protein in the sucrose extract than the other leader peptides analyzed (see FIGS. 2 and 4).

The synthetic leader peptides were then tested at two different arabinose induction concentrations (0.01% and 0.001%) with the cultures grown at 30° C. and shaking at 150 rpm. Samples were harvested 1.5 h and 5 h after arabinose induction. Production levels of the h4D5 scFv in the culture medium, periplasm, and final cell pellets were evaluated by PAGE. The SSS1A and SSS1B leader peptides produced results similar to the StII and OmpA sequences in that a higher molecular weight species (most likely the h4D5 scFv with an unprocessed signal sequence) builds up in the cell pellets with time or at the higher induction concentration. This higher molecular weight species was not observed using the SSS2, SSS2B, or PelB* signal sequences. In general, production levels of h4D5 scFv in the culture medium followed the general trend: SSS2B≅SSS1B>SSS1A≅StII≅OmpA>>PelB*>>SSS2, but the levels can vary depending upon harvest time, induction concentration or growth conditions. The relative differences in scFv levels in the periplasmic fraction were not as pronounced as in the culture medium but also varied somewhat depending on harvest time, growth conditions and induction concentration. In most experiments, the SSS2B leader produced more h4D5 scFv in the periplasm than the other leader peptides.

Figure 5:
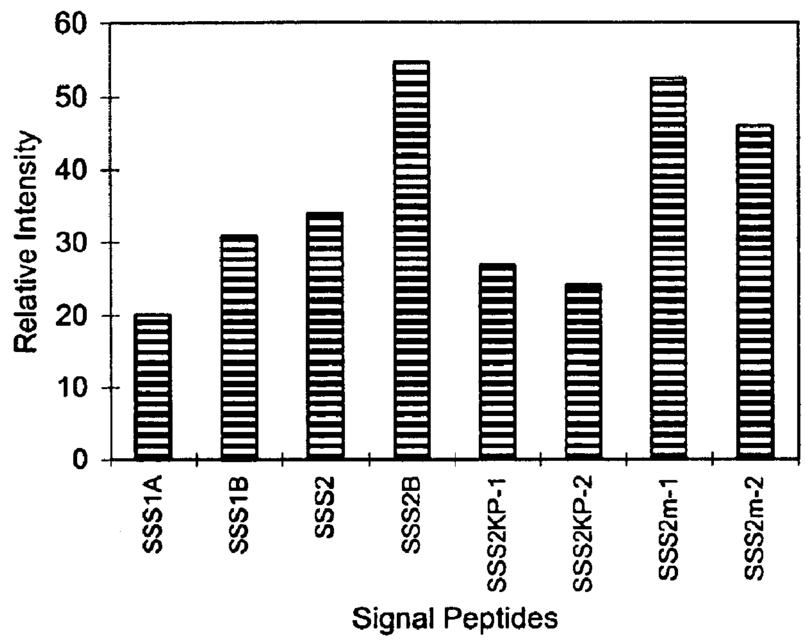
FIG. 5 shows bar graphs of the relative intensity of stained h4D5scFv bands after PAGE of protein samples obtained from bacteria transformed with various leader peptide-h4D5scFv fusions. Protein samples obtained from the sucrose extract and culture medium ("broth") are shown in separate graphs. Ten milliliter cultures were grown for 3.75 hours, induced with arabinose (0.01%), and harvested 5 hours after induction. Samples of 20 μl and 36 μl were loaded of the TCA precipitated surcrose extracts and broth samples, respectively. Two different clones of SSSKP and SSS2m (1 and 2) were tested.
Figure 5:
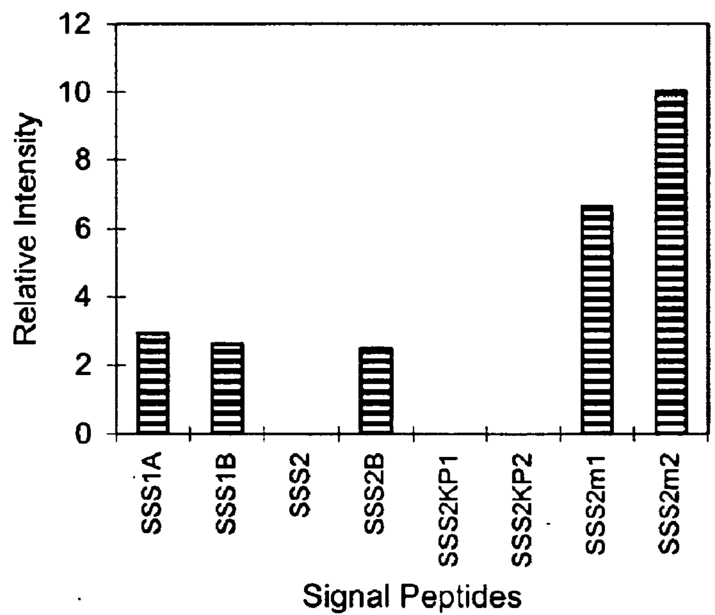

The amino acid sequences of the synthetic leader peptides SSS1A and SSS1B differ only by five amino acids at the end of the hydrophobic core and before the leader peptide cleavage site (ANA), and as might be expected, both of these two leader peptides secrete the 4D5 scFv quite well. However, SSS2 and SSS2B also differ by only five amino acids, but SSS2 produces much less protein in the culture broth than SSS2B. To test whether the difference in production levels was due to the peptide sequence or to the mRNA sequence, two new variants of SSS2, SSS2KP and SSS2m, were made. In SSS2KP, the arginine at position 3 was substituted for a lysine and the asparagine at position 21 for a proline in order to convert the amino acids at these positions to the ones present in the SSS2B leader peptide. In SSS2m, the amino acid sequence of SSS2 was retained, but the wobble positions of six amino acids were changed to alter 5' mRNA structure and/or codon usage. Fusion constructs with h4D5scFv were prepared with each of the new leader peptides as described above. Two independent clones carrying fusion constructs of SSS2KP leader or SSS2m leader were tested against the other four synthetic leader peptides (FIG. 5). SSS2KP functions nearly the same as SSS2, while SSS2m secretes the 4D5 scFv protein as efficiently as SSS2B (under the conditions analyzed in FIG. 5, SSS2m even produces more protein in the culture broth than the other synthetic signal sequences). These results suggest that translation initiation and/or translation elongation of the signal sequences play a role in the efficiency of secretion.

Synthetic Leader Peptide Sequences and Preferred Polynucleotides Encoding Them

```
SSS1A:
CCATGGCTAAAAAGAACTCCACCCTGCTCGTTGCAGTAGCTGCGCTGATCTTCATGGCCGGAAGGGCCAACGCT (SEQ ID NO:9)
   M  A  K  K  N  S  T  L  L  V  A  V  A  A  L  I  F  M  A  G  R  A  N  A  (SEQ ID NO:1)

SSS1B:
CCATGGCTAAAAAGAACTCCACCCTGCTCGTTGCAGTAGCTGCGCTTATCATGTTCACTCAGCCGGCGAACGCT (SEQ ID NO:10)
   M  A  K  K  N  S  T  L  L  V  A  V  A  A  L  I  M  F  T  Q  P  A  N  A  (SEQ ID NO:2)

SSS2:
CCATGGGTCGTAAACAGACCGCTGTTGCATTCGCTCTGGCGCTCCTGTCTCTTGCTTTCACCAACGCGTACGCT (SEQ ID NO:11)
   M  G  R  K  Q  T  A  V  A  F  A  L  A  L  L  S  L  A  F  T  N  A  Y  A  (SEQ ID NO:4)

SSS2B:
CCATGGGTAAGAAACAGACCGCTGTTGCATTCGCTCTGGCGCTCCTGGCTCTTTCTATGACCCCGGCGTACGCT (SEQ ID NO:12)
   M  G  K  K  Q  T  A  V  A  F  A  L  A  L  L  A  L  S  M  T  P  A  Y  A  (SEQ ID NO:3)

SSS2KP:
CCATGGGTAAGAAACAGACCGCTGTTGCATTCGCTCTGGCGCTCCTGTCTCTTGCTTTCACCCCOCCCTACGCT (SEQ ID NO:13)
   M  G  K  K  Q  T  A  V  A  F  A  L  A  L  L  S  L  A  F  T  P  A  Y  A  (SEQ ID NO:14)

SSS2m:
CCATGGGTCGTAAACAGACCGCaGTaGCATTCGCTCTtGCGCTgCTtTCTCTcGCTTTCACCAACGCGTACGCT (SEQ ID NO:15)
   M  G  R  K  Q  T  A  V  A  F  A  L  A  L  L  S  L  A  F  T  N  A  Y  A  (SEQ ID NO:4)
```

Bacterial Signal Sequences

```
StII:
ATGAAAAAGAATATCGCATTTCTTCTTGCATCTATGTTCGTTTTTTCTATTGCTACAAACGCGTACGCT (SEQ ID NO:16)
 M  K  K  N  I  A  F  L  L  A  S  M  F  V  F  S  I  A  T  N  A  Y  A  (SEQ ID NO:17)

PELB*:
CCATGAAATACCTGCTGCCGACCGCTGCTGCTGGTCTGCTGCTCCTCGCTGCCCAGCCGGCGAACGCT  (SEQ ID NO:18)
   M  K  Y  L  L  P  T  A  A  A  G  L  L  L  L  A  A  Q  P  A  N  A   (SEQ ID NO:19)

(*to simplify the construction, the wild type PelB sequence -QPAMA was changed to
-QPANA)

OMPA:
CCATGAAAAAGACAGCTATCGCGATTGCAGTGGCACTGGCTGGTTTCGCTACCGTAGCGCAGGCC     (SEQ ID NO:20)
   M  K  K  T  A  I  A  I  A  V  A  L  A  G  F  A  T  V  A  Q  A      (SEQ ID NO.21)
```

Example 3

Determination of the RNA Secondary Structure of the Fusion Constructs

The predicted secondary structure of the 5' region of mRNA transcribed from each of the fusion constructs was determined using the Genequest program (from the Laser-Gene software from DNASTAR, Inc.). The sequence of the mRNA immediately 5' of the AUG start codon was the same for all of the constructs and was ACCCGTTTTTT-GGGCTAACAGGAGGAATTAACC (SEQ ID NO:22). The sequence of the first 105 bases of the RNA (from the 5' end through the coding region for the leader peptide) was used to predict the RNA secondary structure. Temperature parameter was set at 37° C. and GU pairing was permitted. Table 2 shows the results in terms of the number of bases of the RBS and the AUG that are paired and whether the RBS or the AUG are buried within a stem loop structure.

TABLE 2

| Leader Peptide | RBS base pairs (max = 6) | AUG base pairs (max = 3) | RBS in stem loop | AUG in stem loop |
|---|---|---|---|---|
| SSS1A | 4 | 2 | – | +/– |
| SSS1B | 2 | 1 | – | – |
| SSS2 | 6 | 2 | + | + |
| SSS2B | 5 | 1 | – | + |
| SSS2KP | 6 | 2 | + | + |
| SSS2m | 2 | 0 | – | – |
| OmpA | 2 | 0 | – | – |
| StII | 6 | 0 | + | – |
| PelB | 6 | 0 | + | – |

Example 4

Recombinant Fab' from a Di-cistronic mRNA

A recombinant human immunoglobulin Fab' fragment was expressed in *E. coli* using the synthetic leader sequences to direct secretion of assembled Fab' fragment to the periplasmic space. A DNA sequence was constructed which encoded a di-cistronic message capable of expressing both the heavy and light chains of the Fab' fragment from a single RNA transcript. The coding sequence for a human immunoglobulin kappa chain (Vk1) was placed downstream of, and in frame with, the sequence encoding the SSS2B synthetic leader. Three nucleotides after the translation termination codon of the kappa chain, another initiation of translation signal was inserted, via an NdeI site, in frame with the SSS1A' signal peptide sequence. The heavy chain variable region sequence (VH3) is ligated behind the signal peptide along with a sequence encoding a human CH1 domain and hinge region. Two translation stop signals were included at the end of the coding region to ensure proper termination. The SSS1A' leader peptide has the amino acid sequence MAKKNSTLLVAVAALIFMAGRALA (SEQ ID NO:23), encoded by the nucleotide sequence ATGGCTAAAAAGAACTCCACCCTGCTCGTTGCA-GTAGCTGCGCTGATCTTCATGGCCGGAAGGGCC-TTGGCC (SEQ ID NO:24).

Figure 6:
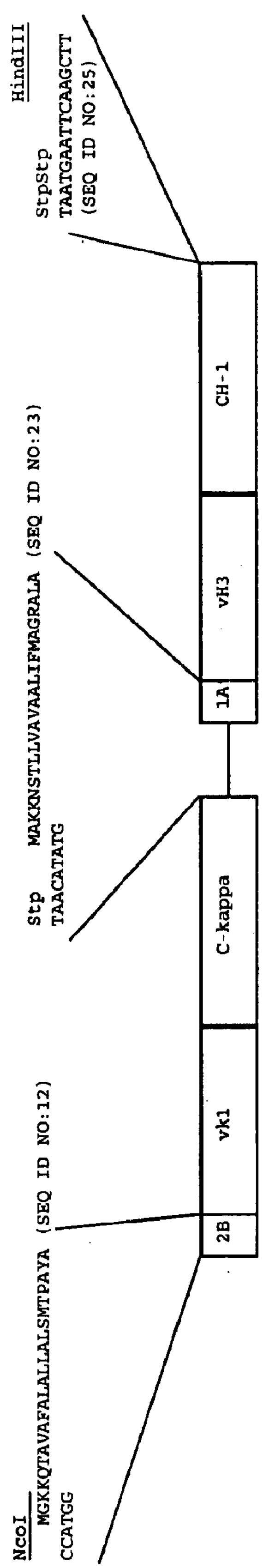
FIG. 6 is a schematic representation of the di-cistronic portion of plasmid pBAD2B1A-vk1-vh3. 2B indicates the SSS2B leader peptide, 1A' indicates that SSS1A' leader peptide. The nucleotide sequence of the intercistronic region is indicated.

The DNA encoding the di-cistronic message was inserted between the NcoI and HinDIII sites of pBADHis (Invitrogen) to form pBAD2B1A-vk1-vh3, such that expression of the di-cistronic message was under the control of the araB promoter. A schematic of the di-cistronic portion of pBAD2B1A-vk1-vh3 is shown in FIG. 6. This plasmid was transformed into the TOP10 *E.coli* strain for characterization and expression. An overnight culture was diluted 1/100 into SuperBroth with 100 1μg/mL of carbenicillin. The culture was allowed to grow at 37° C. in a non-baffled flask at 225 RPM until it reaches an $OD_{600}$ of 0.5 (2–3 hours). At this time, arabinose was added to a final concentration of 0.01%, the temperature was lowered to 30° C., and the culture was allowed to incubate for another 3 hours with shaking. After induction, the bacterial pellet was collected via centrifugation and protein was extracted as described in Example 2. Assembled Fab' fragment, capable of binding to target antigen, was isolated with a yield of approximately 1 mg/l/OD.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the invention.

What is claimed is:

1. An isolated polynucleotide comprising a first nucleotide sequence comprising the coding region for a first leader peptide having the amino acid sequence M-$X_n$-(K/R)-(K/R)-$J_m$-P-$X_p$-Z-X-Z, wherein M is methionine, K is lysine, R is arginine, (K/R) represents either lysine or arginine, P is proline, each X is independently any genetically encoded amino acid, each J is independently an amino acid selected from the group consisting of alanine, leucine, valine, phenylalanine, threonine, isoleucine, seine, glutamine, asparagine, methionine, and tyrosine, each Z is independently an amino acid selected from the group consisting of alanine, seine, glycine, valine and threonine, n is an integer from 1 to 2, p is an integer from 0 to 2, and m is an integer from 7 to 16; and a second nucleotide sequence comprising a first ribosome binding site, wherein said second nucleotide sequence is 5' of said first nucleotide sequence, wherein said first ribosome binding site is operatively joined to said coding region for said first leader peptide, and wherein, when said polynucleotide is RNA or is transcribed into RNA, said first ribosome binding site is accessible.

2. An isolated polynucleotide comprising a first nucleotide sequence comprising a coding region for a first leader peptide having the amino acid sequence of SEQ ID NO: 3; and a second nucleotide sequence comprising a first ribosome binding site wherein said second nucleotide sequence is 5' of said first nucleotide sequence, wherein said first ribosome binding site is operatively joined to said coding region for said first leader peptide, and wherein, when said polynucleotide is RNA or is transcribed into RNA, said first ribosome binding site is accessible.

3. The polynucleotide of claim 2, comprising a nucleotide sequence of SEQ ID NO:7.

4. An expression vector comprising the polynucleotide of claim 1 and a promoter, wherein said promoter is located 5' of and operatively joined to said second nucleotide sequence, whereby the transcription of said first nucleotide sequence is controlled by said promoter.

5. The expression vector of claim 4 wherein said promoter is a bacterial promoter.

6. The expression vector of claim 5, wherein said promoter is selected from the group consisting of the lac promoter, the trp promoter, the ara promoter, the beta-lactamase promoter and the lambda $P_L$ promoter.

7. The polynucleotide of claim 1 or claim 2, further comprising a third nucleotide sequence comprising the coding region for a first recombinant protein, wherein said third nucleotide sequence is 3' of said first nucleotide sequence and is operatively joined to said first nucleotide sequence in such manner that a first fusion polypeptide comprising said first leader peptide joined to said first recombinant protein is encoded.

8. The polynucleotide of claim 7, wherein said first recombinant protein is an immunoglobulin or an immunoadhesin.

9. The polynucleotide of claim 7, wherein said first recombinant protein is an immunoglobulin light chain, an immunoglobulin heavy chain, an immunoglobulin light chain or heavy chain fragment, or a scFv.

10. An expression vector comprising the polynucleotide of claim 7 and a promoter, wherein said promoter is located 5' of and operatively joined to said second nucleotide sequence, whereby the transcription of said first nucleotide sequence and said third nucleotide sequence is controlled by said promoter, resulting in the production of an mRNA encoding said first fusion polypeptide.

11. A method for producing a recombinant protein in a host cell comprising transforming a host cell with the expression vector of claim 10, wherein said promoter is functional in said host cell, culturing said host cell under conditions such that said first fusion polypeptide is expressed and secreted from said host cell, and isolating said first recombinant protein.

12. The method of claim 11, wherein said host cell is a bacterial cell.

13. The polynucleotide of claim 7, further comprising a fourth nucleotide sequence and a fifth nucleotide sequence, wherein said fourth nucleotide sequence is 3' of said third nucleotide sequence, and said fifth nucleotide sequence is 3' of said fourth nucleotide sequence, wherein said fourth nucleotide sequence comprises the coding region for a second leader peptide, having the amino acid sequence M-$X_n$-(K/R)-(K/R)-$J_m$-P-$X_p$-Z-X-Z, wherein M is methionine, K is lysine, R is arginine, (K/R) represents either lysine or arginine, P is proline, each X is independently any genetically encoded amino acid, each J is independently an amino acid selected from the group consisting of alanine, leucine, valine, phenylalanine, threonine, isoleucine, seine, glutamine, asparagine, methionine, and tyrosine, each Z is independently an amino acid selected from the group consisting of alanine, serine, glycine, valine and threonine, n is an integer from 1 to 2, p is an integer from 0 to 2, and m is an integer from 7 to 16; and said fifth nucleotide sequence comprises the coding region for a second recombinant protein, wherein said fourth nucleotide sequence is operatively joined to said fifth nucleotide sequence in such manner that a second fusion polypeptide comprising said second leader peptide joined to said second recombinant protein is encoded, wherein the coding region for said second leader peptide is separated from the coding region for said first recombinant protein by between 1 and 30 nucleotides, and wherein, when said polynucleotide is RNA or is transcribed into RNA, said first ribosome binding site is accessible.

14. The polynucleotide of claim 13, wherein said first recombinant protein and said second recombinant protein are polypeptide subunits of a multimeric protein.

15. The polynucleotide of claim 13, wherein said first recombinant protein and said second recombinant protein are independently selected from the group consisting of an immunoglobulin light chain, an immunoglobulin heavy chain, an immunoglobulin light chain fragment or an immunoglobulin heavy chain fragment.

16. An expression vector comprising the polynucleotide of claim 13 and a promoter, wherein said promoter is located 5' of and operatively joined to said second nucleotide sequence, whereby the transcription of said first nucleotide sequence and said third nucleotide sequence and said fourth nucleotide sequence and said fifth nucleotide sequence is controlled by said promoter, resulting in the production of an mRNA encoding said first fusion polypeptide and said second fusion polypeptide.

17. The expression vector of claim 16, wherein said first recombinant protein and said second recombinant protein are polypeptide subunits of a multimeric protein.

18. The expression vector of claim 16, wherein said first recombinant protein and said second recombinant protein are independently selected from the group consisting of an immunoglobulin light chain, an immunoglobulin heavy chain, an immunoglobulin light chain fragment or an immunoglobulin heavy chain fragment.

19. A method for producing a recombinant protein in a host cell comprising transforming a host cell with the expression vector of claim 16, wherein said promoter is functional in said host cell, culturing said host cell under conditions such that said first fusion polypeptide and said second fusion polypeptide are expressed and secreted from said host cell, and isolating said first recombinant protein and said second recombinant protein.

20. The method of claim 19, wherein said host cell is a bacterial cell.

21. A method for designing a polynucleotide encoding a fusion polypeptide for enhanced secretion of the fusion polypeptide comprising:

(a) selecting a first nucleotide sequence comprising the coding region for a leader peptide having the amino acid sequence M-$X_n$-(K/R)-(K/R)-$J_m$-P-$X_p$-Z-X-Z, wherein M is methionine, K is lysine, R is arginine, (K/R) represents either lysine or arginine, P is proline, each X is independently any genetically encoded amino acid, each J is independently an amino acid selected from the group consisting of alanine, leucine, valine, phenylalanine, threonine, isoleucine, serine, glutamine, asparagine, methionine, and tyrosine, each Z is independently an amino acid selected from the group consisting of alanine, serine, glycine, valine and threonine, n is an integer from 1 to 2, p is an integer from 0 to 2, and m is an integer from 7 to 16;

(b) selecting a second nucleotide sequence comprising a ribosome binding site, wherein said second nucleotide sequence is joined to said first nucleotide sequence such that said second nucleotide sequence is 5' of said first nucleotide sequence, and wherein when said joined first and second nucleotide sequence is RNA or is transcribed into RNA, said ribosome binding site is accessible;

(c) selecting a third nucleotide sequence encoding a recombinant protein, wherein said third nucleotide sequence is joined to said first nucleotide sequence in such manner that a fusion polypeptide comprising said leader peptide joined to said recombinant protein is encoded; and (d) assembling said selected first, second and third nucleotide sequences into a single polynucleotide.

* * * * *